US012178743B1

(12) United States Patent
Blaylock et al.

(10) Patent No.: US 12,178,743 B1
(45) Date of Patent: Dec. 31, 2024

(54) PVC HEATING BLANKET

(71) Applicant: TEMCo Industrial, LLC, Fremont, CA (US)

(72) Inventors: Bryan C. Blaylock, Fremont, CA (US); Josh L. Leber, Fremont, CA (US)

(73) Assignee: TEMCO INDUSTRIAL, LLC, Fremont, CA (US)

( * ) Notice: Subject to any disclaimer, the term of this patent is extended or adjusted under 35 U.S.C. 154(b) by 0 days.

(21) Appl. No.: 18/406,661

(22) Filed: Jan. 8, 2024

(51) Int. Cl.
*A61F 7/00* (2006.01)
*H05B 3/34* (2006.01)
*H05B 3/36* (2006.01)

(52) U.S. Cl.
CPC .......... *A61F 7/0097* (2013.01); *H05B 3/342* (2013.01); *H05B 3/36* (2013.01)

(58) Field of Classification Search
CPC .. A61F 7/0097; A61F 7/08; A61F 2007/0228; A61F 2007/0231; H05B 3/342; H05B 3/36; H05B 3/0052; H05B 3/0042; H05B 3/0038; H05B 3/0071; H05B 3/18; H05B 3/34; H05B 3/345; H05B 3/347; H05B 1/0236; H05B 1/025; H05B 1/0252; H05B 1/0272; H05B 1/0291; H05B 1/0294; H05B 1/0244; H05B 2203/002; H05B 2203/003; H05B 2203/004; H05B 2203/01; H05B 2203/011; H05B 2203/013; H05B 2203/015; H05B 2203/022; H05B 2203/036
See application file for complete search history.

(56) References Cited

U.S. PATENT DOCUMENTS 3,889,101 A * 6/1975 Woods .................... A61F 7/007 604/291
5,714,738 A * 2/1998 Hauschulz ............. F16L 53/35 219/535
5,910,266 A * 6/1999 Jones ....................... H05B 3/58 219/535
6,969,831 B1 * 11/2005 Parker .................... H05B 3/342 219/528

(Continued)

FOREIGN PATENT DOCUMENTS

EP 0746962 B1 * 8/2003
GB 2442094 A * 3/2008 ............ A61F 7/007

OTHER PUBLICATIONS

Photograph of Greenlee Heating Blanket.
Screen shot of Current Tools PVC Heating Blanket, https://www.amazon.com/CURRENT-Heating-Blanket-Conduit-Bending/dp/B00J9RXZB6/ref=asc_df_B00J9RXZB6/?tag=hyprod-20&linkCode=df.

*Primary Examiner* — Shawntina T Fuqua
(74) *Attorney, Agent, or Firm* — Donald J. Ersler

(57) ABSTRACT

A PVC heating blanket preferably includes a power unit, a heating blanket portion, and a fastening device. The power unit preferably includes a thermostat and a power cord. The thermostat controls the flow of electrical current to the heating blanket portion. If the heating blanket portion gets too hot, the thermostat will stop the flow of electrical current to the heating blanket portion. The heating blanket portion preferably includes a heating element and a flexible outer cover. The heating element is retained within the flexible cover. The fastening device extends from a middle of one edge of the heating blanket portion. The power unit is located adjacent the one edge of the heating blanket portion.

20 Claims, 5 Drawing Sheets

(56) References Cited

U.S. PATENT DOCUMENTS

| | | | | |
|---|---|---|---|---|
| 2007/0181562 | A1* | 8/2007 | Cardenas | H05B 3/56 219/549 |
| 2012/0279953 | A1* | 11/2012 | Augustine | A61F 7/08 219/217 |
| 2014/0074196 | A1* | 3/2014 | Barnett | A61F 7/08 607/96 |
| 2018/0168854 | A1* | 6/2018 | Barnett | H05B 3/34 |
| 2024/0077161 | A1* | 3/2024 | Sandoval | F16L 59/22 |

* cited by examiner

PVC HEATING BLANKET

BACKGROUND OF THE INVENTION

1. Field of the Invention

The present invention relates generally to the building trades and more specifically to a PVC heating blanket, which includes a power unit located adjacent one edge of the heating blanket and a fastening device extending from the one edge of the heating blanket.

2. Discussion of the Prior Art

In order to bend a PVC tube, it must be first heated. Otherwise, PVC tube will break or kink when bent. Prior art PVC heating blankets locate a power unit, adjacent one edge and a fastening strap on an opposing edge. Locating the power unit on one edge and the fastening strap on an opposing edge has the disadvantage of decreasing surface area contact of the heating blanket portion with the PVC tube. The result is electricity wasted and a longer time to heat the PVC tube. Further, the power unit includes an electrical cord. Prior art PVC heating blankets locate the power cord on an edge of a perimeter of the heating blanket portion. The result is that the packaging which stores the PVC heating blanket must be longer to accommodate a width of the electrical cord. Further, there must be additional packaging material used and increased shelf space to store the PVC heating blanket packaging.

Accordingly, there is a clearly felt need in the art for a PVC heating blanket, which includes a power unit located, adjacent one edge of a heating blanket portion, and a fastening device extending from the one edge of the heating blanket portion; and a power unit offset from a perimeter edge of the heating blanket portion to provide clearance for at least a width of the electrical cord.

SUMMARY OF THE INVENTION

The present invention provides a PVC heating blanket, which includes a power unit offset from a perimeter edge of the heating blanket portion to provide clearance for at least a width of the electrical cord. The PVC heating blanket preferably includes a power unit, a heating blanket portion, and a fastening device. The power unit preferably includes a thermostat and a power cord. The thermostat controls the flow of electrical current to the heating blanket portion. If the heating blanket portion gets too hot, the thermostat will stop the flow of electrical current to the heating blanket portion. The heating blanket portion preferably includes a heating element and a flexible outer cover. The heating element is preferably a long filament, which has a looped pattern to cover an inner surface area of the heating blanket portion. The flexible outer cover is heat conductive, but not electrically conductive. The heating element is retained within the flexible cover. The fastening device extends from a middle of one edge of the heating blanket portion. The fastening device is preferably a fastening strap, but could be any other suitable fastening device. The fastening strap preferably includes hook and loop fasteners. The power unit is located adjacent the one edge of the heating blanket portion, and the fastening device. In use, an edge opposite the one edge of the heating blanket portion is put in contact with the PVC tube and wrapped around the PVC tube. The heating blanket portion is secured in place by wrapping the fastening strap around the heating blanket portion and securing thereof to itself. The power cord is then plugged into an 120 VAC electrical socket to heat the PVC tube.

Accordingly, it is an object of the present invention to provide a PVC heating blanket with a power unit located adjacent one edge of a heating blanket portion and a fastening device extending from the one edge of the heating blanket portion.

Finally, it is another object of the present invention to provide a PVC heating blanket with a power unit, which is offset from a perimeter edge of the heating blanket portion to provide clearance for at least a width of the electrical cord.

These and additional objects, advantages, features and benefits of the present invention will become apparent from the following specification.

DETAILED DESCRIPTION OF THE PREFERRED EMBODIMENTS

Figure 1:
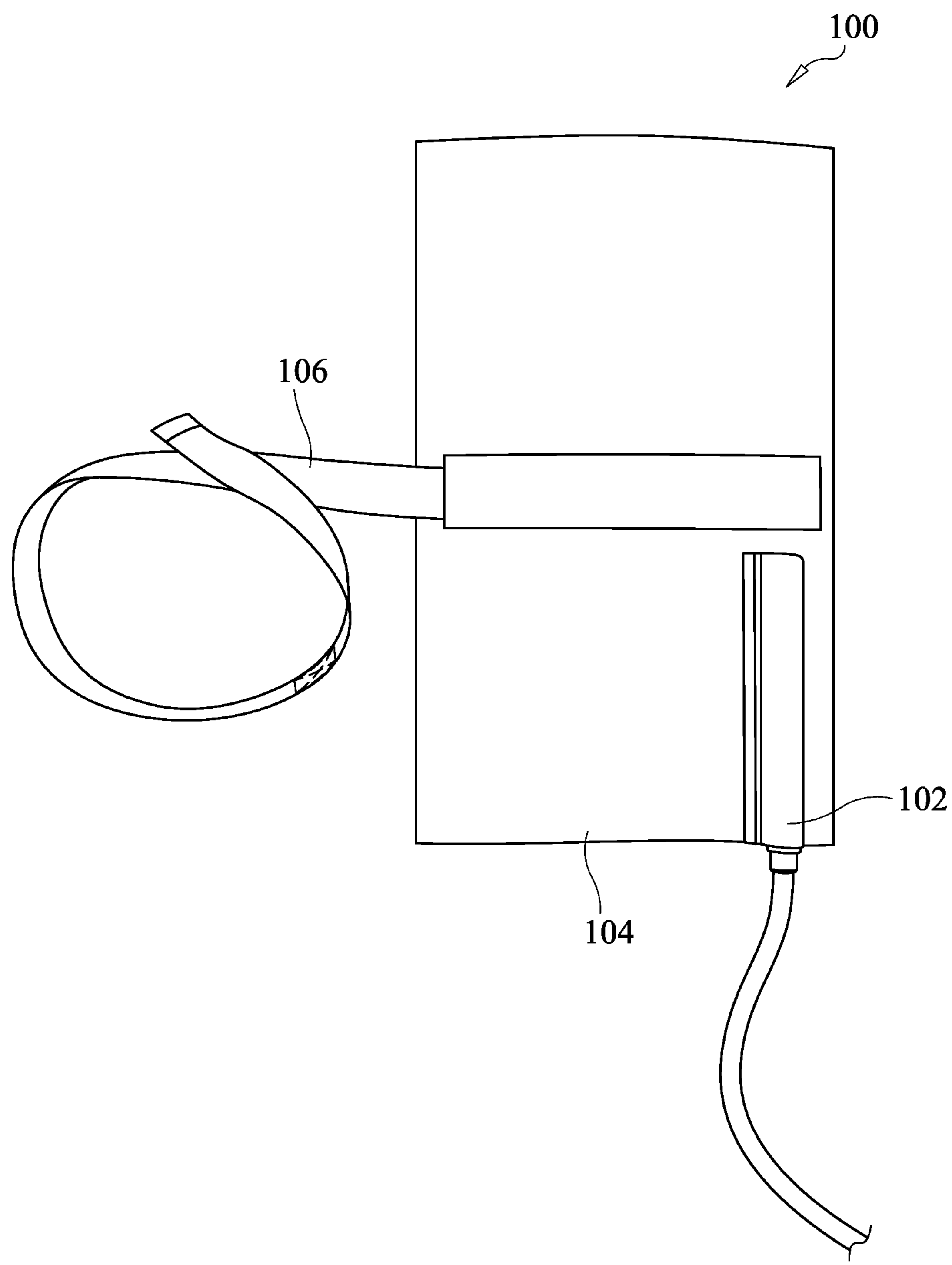
FIG. 1 is a top view of a prior art PVC heating blanket.
Figure 2:
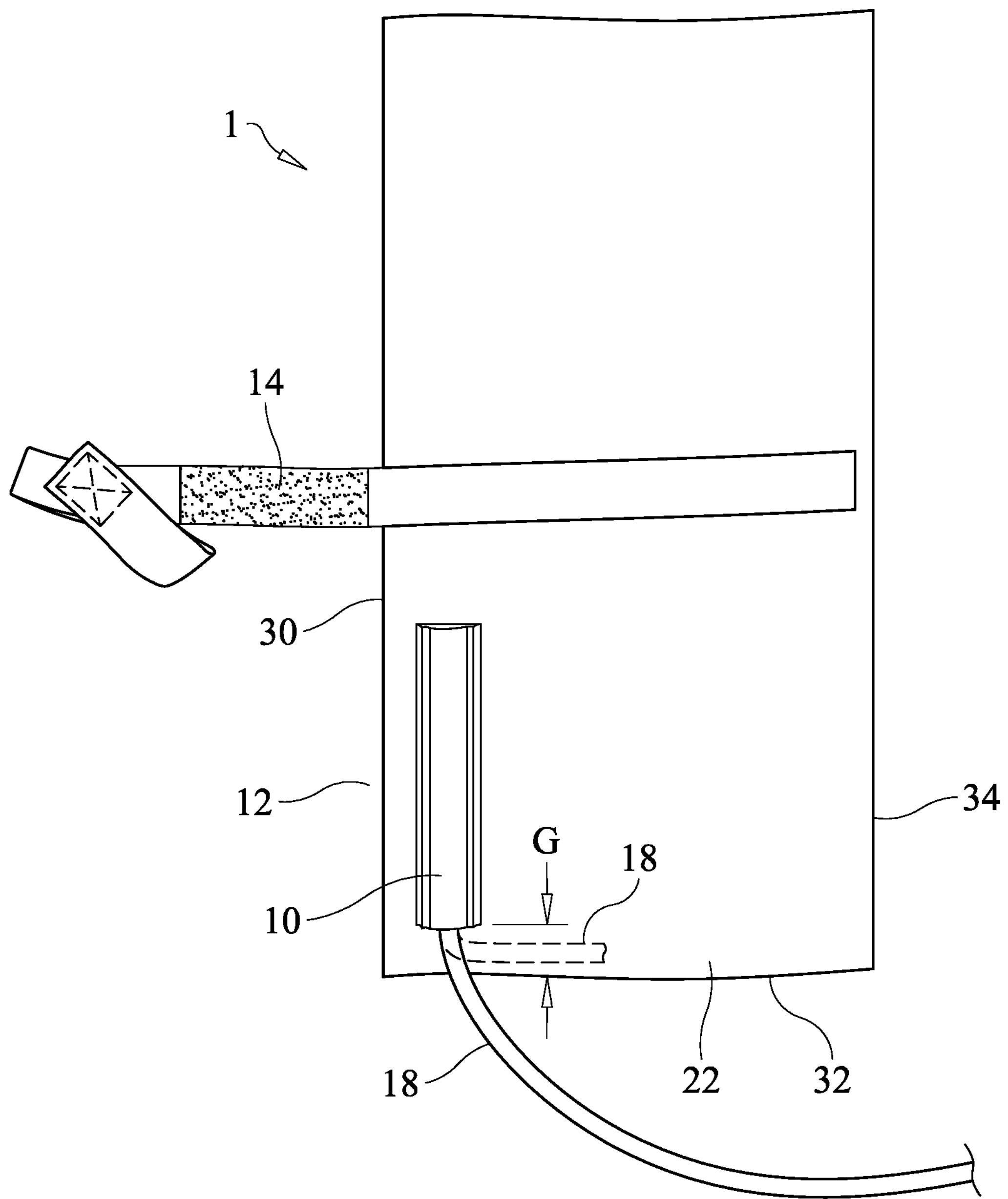
FIG. 2 is a top view of a PVC heating blanket in accordance with the present invention.
Figure 3:
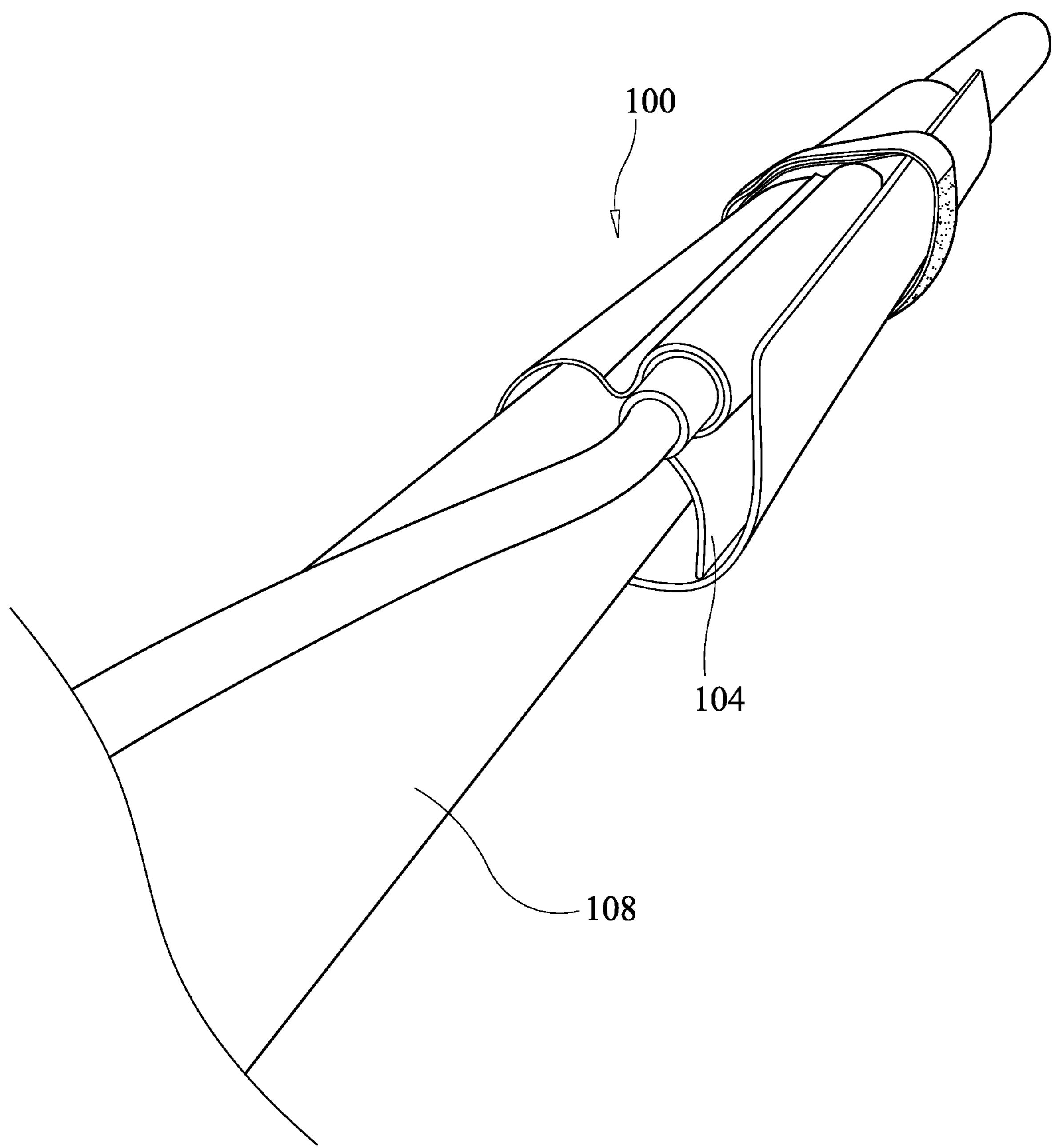
FIG. 3 is a perspective view of a prior art PVC heating blanket wrapped around a PVC tube.
Figure 4:
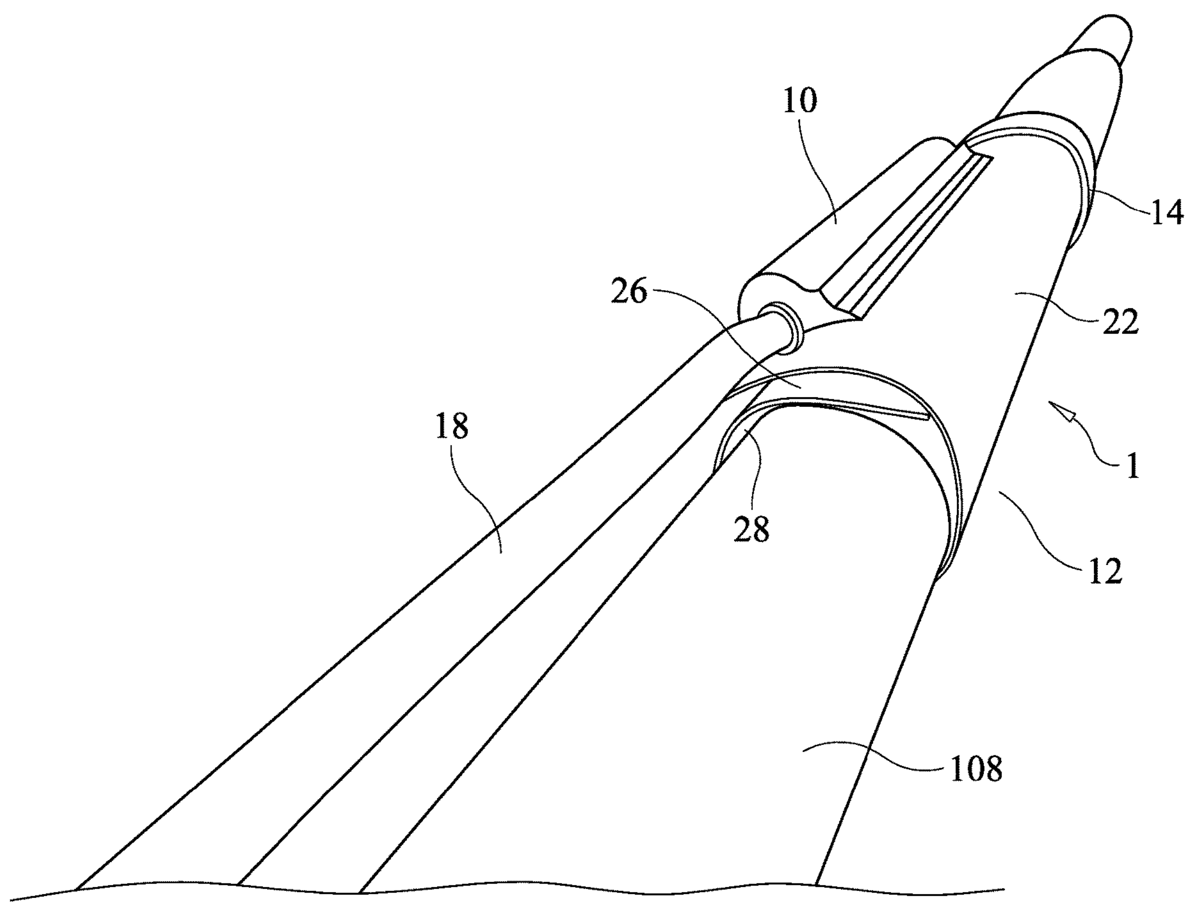
FIG. 4 is a perspective view of a PVC heating blanket wrapped around a PVC tube in accordance with the present invention.

With reference now to the drawings, and particularly to FIG. 2, there is shown a top view of a PVC heating blanket 1. With reference to FIG. 1, a prior art PVC heating blanket 100 is shown. The PVC heating blanket 100 includes a power unit 102, a heating blanket portion 104 and a fastening strap 106. The power unit 102 is located, adjacent one edge of the heating blanket portion 104 and the fastening strap 106 extends from an opposing edge of the heating blanket portion 104. With reference to FIG. 3, the PVC heating blanket 100 is secured to a PVC tube 108. The end of the heating blanket portion 104 is wrapped around an outer perimeter of the power unit 102 instead of the heating blanket portion 104 or the PVC tube 108. With reference to FIG. 4, PVC heating blanket 1 is wrapped around the PVC tube 108 or a heating blanket portion 12, because of the location of a power unit 10 relative to a fastening device 14.

Figure 5:
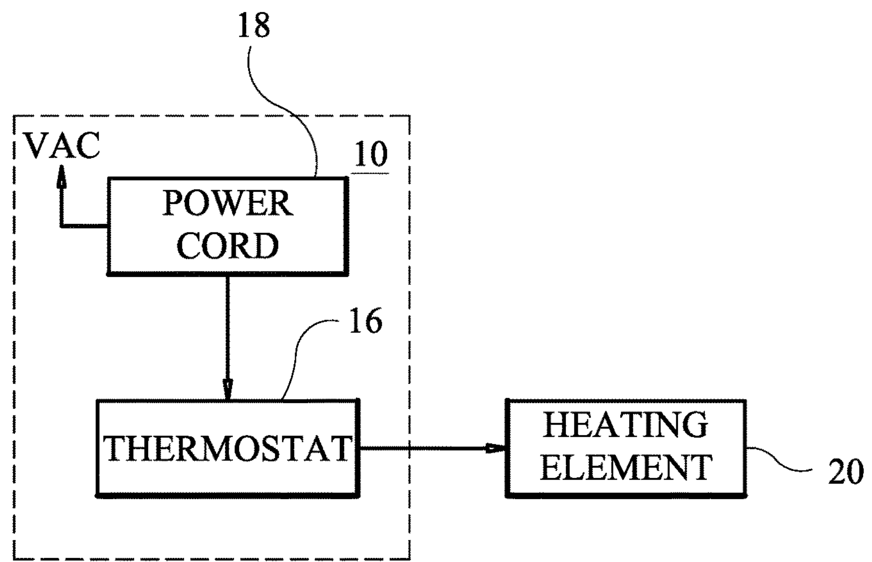
FIG. 5 is a schematic diagram of a preferred power unit of a PVC heating blanket in accordance with the present invention.
Figure 6:
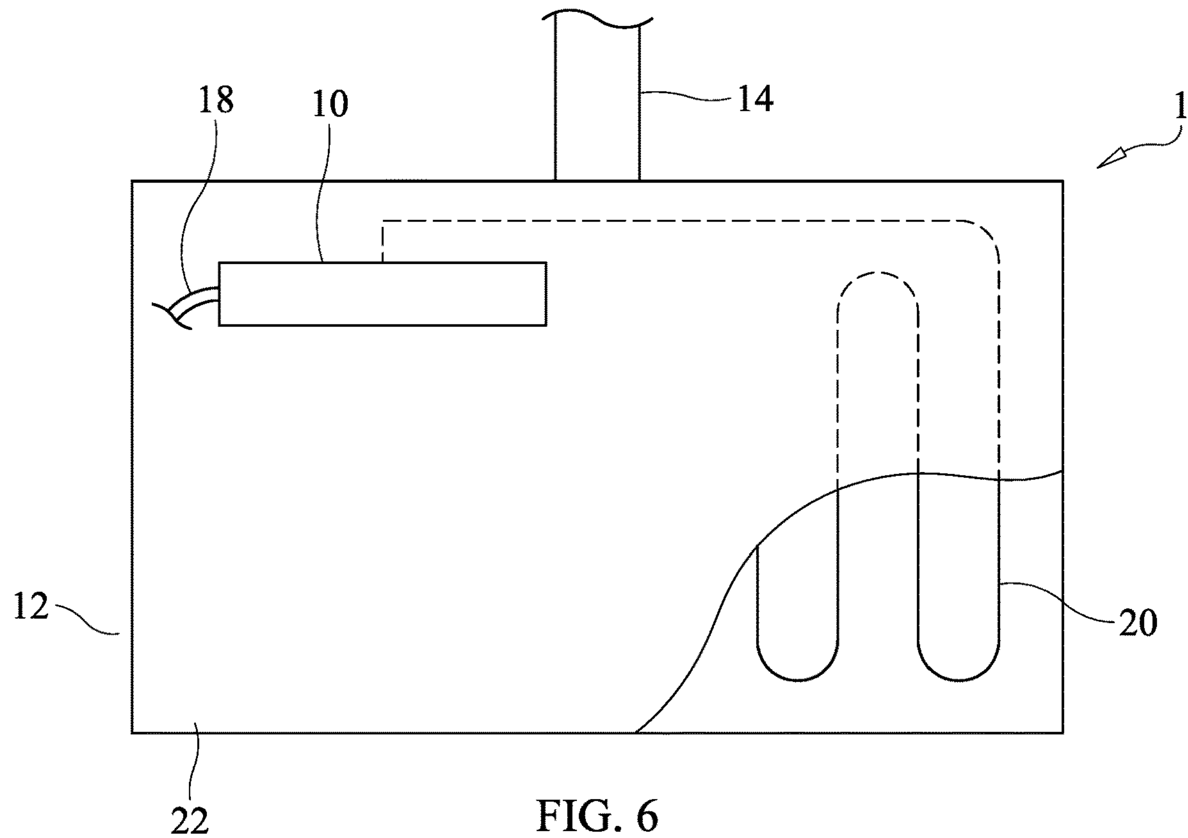
FIG. 6 is a top view of a heating blanket portion with a portion of a flexible cover removed to illustrate a heating element of a PVC heating blanket in accordance with the present invention.

The PVC heating blanket 1 preferably includes the power unit 10, the heating blanket portion 12, and the fastening device 14. With reference to FIG. 5 the power unit 10 preferably includes a thermostat 16 and a power cord 18. The thermostat 16 and the heating element 20 are powered by 120 VAC. The thermostat 16 controls the flow of electrical current to the heating blanket portion 12. If the heating blanket portion 12 gets too hot, the thermostat 16 will stop the flow of electrical current to the heating blanket portion 12. The heating blanket portion 12 preferably includes a heating element 20 and a flexible outer cover 22. The heating element 20 is preferably a long electrically conductive filament, which has a looped pattern to cover an inner surface area of the heating blanket portion 12. The flexible outer cover 22 includes a top layer 26 and a bottom layer 28.

The flexible outer cover 22 is fabricated from a flexible material which is heat conductive, but not electrically conductive. The heating element 20 is retained between the top layer 26 and the bottom layer 28 of the flexible outer cover 22. The fastening device 14 extends from a middle of one edge 30 of the heating blanket portion 12. The fastening device 14 is preferably a fastening strap, but could be any other suitable fastening device. The fastening strap preferably includes hook and loop fasteners. The hook and loop fasteners are a Velcro® product, but other types of straps could also be used. The power unit 10 is located adjacent the one edge 30 of the heating blanket portion 12. A gap G exists between a side edge 32 of the heating blanket portion 12 and an end of the power unit 10. The gap G allows the electrical cord 18 to be pushed inside a perimeter of the heating blanket portion 12, when the PVC heating blanket 1 is placed in packaging, such as a box. The gap G also assists a user in getting an edge of the PVC heating blanket as close to a wall as possible, without the power cord 18 acting as an obstruction. The gap G is at least a thickness of the power cord 20. In use, an edge 34 opposite the one edge 30 of the heating blanket portion 12 is put in contact with the PVC tube 108 and wrapped around the PVC tube 108. The heating blanket portion 12 is secured in place by wrapping the fastening strap 14 around the heating blanket portion 12 and securing thereof to itself. The power cord 18 is then plugged into an 120 VAC electrical socket to heat the PVC tube 108.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

We claim:

1. A PVC heating blanket, comprising:

a power unit includes a thermostat, said thermostat receives electrical power from a source of electrical current;

a heating blanket portion includes an outer cover and a heating element, a thickness of said heating blanket portion allows thereof to be overlapped to accommodate different diameters of pipe, said heating element is contained within said outer cover said outer cover includes an outer perimeter, a bottom surface of said power unit is attached to an outer planar surface of said outer cover, said power unit is located adjacent one edge of said outer perimeter; and a fastening device includes a free end, said free end extends from said one edge of said outer perimeter.

2. The PVC heating blanket of claim 1, wherein:

said heating element includes an electrically conductive filament having a looped pattern.

3. The PVC heating blanket of claim 1, further comprising:

said power source is an AC voltage.

4. The PVC heating blanket of claim 1, wherein:

said outer cover is fabricated from a flexible material.

5. The PVC heating blanket of claim 1, wherein:

said outer cover is not electrically conductive.

6. The PVC heating blanket of claim 1, wherein:

said fastening device is a fastening strap.

7. The PVC heating blanket of claim 6, wherein:

said fastening strap includes hook and loop fasteners.

8. A PVC heating blanket, comprising:

a power unit includes a thermostat and a power cord, said power cord includes a cord free end, said thermostat receives electrical power from a source of electrical current through said power cord;

a heating blanket portion includes an outer cover and a heating element, said heating element is contained within said outer cover, said outer cover includes an outer perimeter, a bottom of said power unit is attached to an outer planar surface of said outer cover, said free end of said power cord extends from an end of said power unit, a distance between an end of said power unit and said outer perimeter of said heating blanket portion is at least a thickness of said cord free end of said power cord, said power unit is located within an outer perimeter of said heating blanket portion, said power cord extends from said power unit, a lengthwise axis of said power cord is parallel to a plane of said of heating blanket; and a fastening device includes a fastener free end, said fastener free end extends from said one edge of said outer perimeter.

9. The PVC heating blanket of claim 8, wherein:

said heating element includes an electrically conductive filament having a looped pattern.

10. The PVC heating blanket of claim 8, further comprising:

said power source is an AC voltage.

11. The PVC heating blanket of claim 8, wherein:

said outer cover is fabricated from a flexible material.

12. The PVC heating blanket of claim 8, wherein:

said outer cover is not electrically conductive.

13. The PVC heating blanket of claim 8, wherein:

said fastening device is a fastening strap.

14. The PVC heating blanket of claim 13, wherein:

said fastening strap includes hook and loop fasteners.

15. A PVC heating blanket, comprising:

a power unit includes a thermostat and a power cord, said power cord includes a cord free end, said thermostat receives electrical power from a source of electrical current through said power cord;

a heating blanket portion includes an outer cover and a heating element, a thickness of said heating blanket portion allows thereof to be overlapped to accommodate different diameters of pipe, said outer cover includes a top layer and a bottom layer, said heating element is contained between said top and bottom layers, a bottom of said power unit is attached to an outer planar surface of said outer cover, said outer cover includes an outer perimeter, said power unit is located adjacent one edge of said outer perimeter, said cord free end of said power cord extends from an end of said power unit, a distance between an end of said power unit and said outer perimeter of said heating blanket portion is at least a thickness of said cord free end of said power cord, said power unit is located within an outer perimeter of said heating blanket portion, said power cord extends from said power unit, a lengthwise axis of said power cord is parallel to a plane of said of heating blanket; and a fastening device includes a fastener free end, said fastener free end extends from said one edge of said outer perimeter.

16. The PVC heating blanket of claim 15, wherein:

said heating element includes an electrically conductive filament having a looped pattern.

17. The PVC heating blanket of claim 15, further comprising:

said power source is an AC voltage.

18. The PVC heating blanket of claim 15, wherein: said outer cover is fabricated from a flexible material.

19. The PVC heating blanket of claim 15, wherein: said outer cover is not electrically conductive.

20. The PVC heating blanket of claim 15, wherein: said fastening strap includes hook and loop fasteners.

* * * * *